United States Patent [19]

Farrell

[11] Patent Number: 4,687,745
[45] Date of Patent: Aug. 18, 1987

[54] USE OF RLDM ™ 1-6 AND OTHER LIGNINOLYTIC ENZYMES IN THE TREATMENT OF MECHANICAL PULPS

[75] Inventor: Roberta L. Farrell, Danvers, Mass.

[73] Assignee: Repligen Corporation, Cambridge, Mass.

[21] Appl. No.: 845,656

[22] Filed: Mar. 28, 1986

Related U.S. Application Data

[63] Continuation-in-part of Ser. No. 755,244, Jul. 15, 1985, abandoned.

[51] Int. Cl.$^4$ .................. D21C 3/00; D21C 3/20; C12R 1/645
[52] U.S. Cl. ........................ 435/278; 162/72; 435/911
[58] Field of Search ............ 162/72; 435/278, 277

[56] References Cited

PUBLICATIONS

Casey, J. P. (1983) "Mechanical and Chemimechanical Pulping: a Perspective" *Tappi Journal* 66(6):95–96.
Springer, E. L. (1983) "Evaluation of Chemical Treatments for Maintaining Brightness of Stored Wood Chips" *Tappi Journal* 66(2):93–96.
Rapson, W. H. (1969), "Mechanisms of Groundwood Bleaching" *Appitta* 23(2):102–114.
Higuchi, T. (1982), "Biodegradation of Lignin: Biochemistry and Potential Applications" *Experientia* 38:159–166.
Pilon, L. Desrochers, M., Jurasek, L. and Neumann, P. J. (1982), "Increasing Water Retention of Mechanical Pulp by Biological Treatments" *Tappi Journal* 65(6):93–96.
Alberti, B. N. and Klibanov, A. M. (1981), "Enzymatic Removal of Dissolved Aromatics from Industrial Aqueous Effluents" *Biotechnology and Bioengineerng Symp.* 11:373–379.

*Primary Examiner*—Lionel M. Shapiro
*Attorney, Agent, or Firm*—Roman Saliwanchik; David R. Saliwanchik

[57] ABSTRACT

Disclosed is a novel process for enhancing the strength properties and brightness stability of mechanical pulps. The process uses novel enzymes called rLDM ™ and other ligninolytic enzymes present in the extracellular growth medium of a fermentation of *Phanerochaete chrysosporium*.

23 Claims, No Drawings

USE OF RLDM ™ 1-6 AND OTHER LIGNINOLYTIC ENZYMES IN THE TREATMENT OF MECHANICAL PULPS

CROSS REFERENCE TO A RELATED APPLICATION

This is a continuation-in-part of my copending application Ser. No. 755,244, filed July 15, 1985, now abandoned.

BACKGROUND OF THE INVENTION

The objective of mechanical pulping is to produce high-yield pulps. Several years ago mechanical pulping was limited to a single process, the grinding of roundwood against a pulpstone, but since then mechanical pulping has expanded into an array of processes that use chemical, thermal and compression technologies (Casey, J. P. [1983] Tappi Journal 66:95-96). A drawback to the current methods used is that they produce pulp with poor bonding strength and poor brightness stability.

Thermomechanical pulp (TMP), chemithermomechanical pulp (CTMP) and chemimechanical pulp (CMP) processes have evolved to improve mechanical pulp quality, expanding its utility in end product applications. Thermomechanical pulping is the dominant alternative high-yield pulping process. Its major limitation is the requirement for high electrical energy input, most of which ends up as low grade heat.

The utilization of thermomechanical pulps would be greatly facilitated if there was an increase of strength properties and if the stability of brightening could be enhanced, i.e., prevent brightness reversion. Brightness reversion of commercial pulps can be related to the presence of oxidized groups. These groups are principally derived from the residual breakdown products of lignin. It is postulated that the introduction of aldehyde and ketone groups into cellulose upon bleaching also contributes to brightness reversion, although to a lesser extent (Springer, E. L. [1983] Tappi Journal 66:93-96.). Breakdown products of lignin cause brightness reversion by mechanisms that are now being elucidated in several laboratories. It has been postulated that $\alpha$-carboxyl groups adjacent to aromatic rings in residual lignin absorb daylight and transfer this energy to oxygen which in turn reacts with the phenolic groups of the lignin leading to formation of colored (yellow) quinones (Rapson, W. H. [1969] Appita 23:102-114). This reaction can occur only on "exposed" lignin rings which contain a free hydroxyl group.

Foremost in preventing brightness reversion is the necessity to modify lignin by oxidative cleavage of the exposed aromatic rings so that they cannot form quinones. This should drastically reduce brightness reversion properties.

Coarse TMP can be produced with relatively low inergy input. Subsequent secondary refining, however, requires substantial energy for development of pulp properties (Higuchi, T. [1982] Experientia 38:159-166). Experiments have demonstrated (Pilon, L., Desrochers, M., Jurasek, L., Neuman, P. J. [1982] Tappi Journal 65:93-96) that treatment of coarse TMP with P. chrysosporium cultures for 14 days can substantially reduce the energy requirement for secondary refining without a loss in pulp quality. Preliminary studies showed that the energy requirements to develop a given freeness in fungal-treated pulp was reduced by 25-30% as compared to untreated pulps Furthermore, pulp properties, as measured by the burst index, were also improved considerably. Because the refining of mechanical pulps after swelling in alkali can ccnsiderably improve strength properties, both the fungus-treated and untreated pulps were subjected to refining after swelling in alkali. The fungus-treated pulp then required 50% less refining energy than did the untreated pulp without any loss in strength properties.

In related experiments (Alberti, B. N. and Klibanov, A. M. [1981] Biotech. and Bioeng. Symp. 11:373-379), the water retention value (WRV) of fungal-treated pulps was tested in order to evaluate the effects of biological treatment on mechanical pulps. The WRV is a measure of the swelling and flexibility of the fibers. Increased swelling indicates greater contact between fibers during papermaking, this increasing the strength. An 88% gain in WRV was obtained after pretreatment of pulp with Schizophyllum commune, another white rot fungus, over untreated pulps.

The technical problems in applying organisms to industrial mechanical pulps, including TMP processing, are threefold: (a) in scaling-up with the required careful control of humidity, aeration and temperature; (b) in preventing contamination by unwanted organisms; and (c) in the impractical slowness of lignin degradation.

BRIEF SUMMARY OF THE INVENTION

The subject invention concerns the enhancement of the strength properties of mechanical pulps, including TMP, CTMP, and CMP, by treating them with rLDM ™ and other ligninolytic enzymes present in the extracellular growth medium from a fermentation of *Phanerochaete chrysosporium*. The rLDM ™ selectively degrade only the chemical moieties formed in lignin and will not degrade cellulose or hemicellulose.

rLDM ™ can enhance the strength properties of these pulps and they are immediately active. Thus, there is no lag in activity as with fungal cultures. Since the rLDM ™ are biological molecules, they are, advantageously, not corrosive, do not cause pollution, and do not present an environmental hazard when released.

The lignin-degrading enzymes of the invention, referred to as rLDM ™, are referred to as Pulpases ™ in co-pending application Ser. No. 755,244.

DETAILED DESCRIPTION OF THE INVENTION

The rLDM ™ which can be used in the subject invention process were isolated from a novel stable mutant strain of the white-rot fungus *Phanerochaete chrysosporium*. The novel mutant strain, designated SC26, has been deposited in the permanent collection of a public culture repository, to be maintained for at least 30 years. The culture repository is the Northern Regional Research Laboratory, U.S. Department of Agriculture, Peoria, Illinois 61604, USA. The accession number is NRRL 15978, and the deposit date is July 3, 1985. This deposited culture is available to the public upon the grant of a patent disclosing it. The deposit also is available as required by foreign patent laws in countries wherein counterparts of the subject application, or its progeny, are filed. However, it should be understood that the availability of a deposit does not constitute a license to practice the subject invention in derogation of patent rights granted by governmental action.

Novel mutant SC26 was obtained by UV mutagenesis of the wild type *Phanerochaete chrysosporium*, ATCC 24725.

Novel mutant SC26 was grown on a nitrogen-limited trace element medium supplemented with glucose and buffered at pH 4.5.

Ligninase activity in the fermentation medium was measured periodically by standard means determining the rate of oxidation of veratryl alcohol to veratrylaldehyde.

Isolation and purification of the ligninases from the extracellular fluid in the fermentation was accomplished by ultrafiltration and fast protein liquid chromatography (FPLC) using an anion exchange column.

The rLDM TM used in the subject invention process were prepared as follows:

PREPARATIVE

EXAMPLE 1 GROWTH OF MUTANT SC26 (NRRL 15978) TO PRODUCE FERMENTATION MEDIUM CONTAINING NOVEL LIGNINASES

Inoculum was prepared by homogenizing 50 ml of 1.5 day cultures of mutant SC26 grown in 1 liter flasks containing the following medium, designated nitrogen-limited BIII/glucose medium:

The BIII medium contains $1.08 \times 10^{-3}$M ammonium tartrate, $1.47 \times 10^{-2}$M $KH_2PO_4$, $2.03 \times 10^{-3}$M $MgSO_4.7H_2O$, $6.8 \times 10^{-4}$M $CaCl_2 2H_2O$, $2.96 \times 10^{-6}$M thiamine·HCl and 10 ml·L$^{-1}$ of a trace element solution. The trace element solution contains .$7H_2O$, $1.7 \times 10^{-2}$M NaCl, $3.59 \times 10^{-4}$M $FeSO_4.7H_2O$, $7.75 \times 10^{-4}$M $CoC_2$, $9.0 \times 10^{-4}$M $CaCl_2$, $3.48 \times 10^{-4}$M $ZnSO_4 \cdot 7H_2O$, $4 \times 10^{-5}$M $CuSO_4.5H_2O$, $2.1 \times 10^{-5}$M $AlK(S_4)_2O$, $1.6 \times 10^{-4}$M $H_3BO_3$, $4.1 \times 10^{-5}$M $NaMoO_4.2H_2O$ and $2.9 \times 10^{-3}$M $MnSO_4.H_2O$.

The medium was supplemented with 10% (by wt/liter) of glucose.

The medium was buffered with 10 mM trans-aconitic acid, pH 4.5.

Flasks (125 ml, containing 10 ml sterile medium having the above-described medium) were each inoculated with 0.5 ml of the above homogenate and kept stationary at 39° C. The flasks were flushed on days 0, 3, and 6 with water-saturated $O_2$. Alternatively, a rotating biological contractor (RBC) was used to grow the fungus. 2.5 liters of the above-described medium was inoculated with 100 ml of the above homogenate and grown at 39° C. with the RBC rotating at 1 rpm with continuous oxygenation.

Ligninase activity was measured periodically by determining the rate of oxidation of veratryl alcohol to veratrylaldehyde. Reaction mixtures contained 275 μl of extracellular fluid (from flasks or the RBC), 2 mM veratryl alcohol, 0.4 mM $H_2O_2$ and 0.1 mM sodium tartrate, pH 2.5 in a final volume of 0.5 ml. The reactions were started by $H_2O_2$ addition immediately after buffer was added and were monitored at 310 nm. Protein was determined according to Bradford (Bradford, M. M. [1976] Anal. Biochem. 72:248-254). using bovine serum albumin (Sigma Chemical, St. Louis, MO) as standard.

PREPARATIVE

EXAMPLE 2—ISOLATION AND PURIFICATION OF THE NOVEL rLDM TM

The extracellular growth media from cultures grown in flasks, as described above, was harvested by centrifugation at 5000×G, 10 min., 4° C. Extracellular growth media was then concentrated by ultrafiltration through a 10K filter. The resulting concentrate is called the Ligninolytic Mixture TM. The rLDM TM contained in this Ligninolytic Mixture TM were separated by fast protein liquid chromatography (FPLC) using a Pharmacia Mono Q column (Pharmacia, Piscataway, NJ) and a gradient of sodium acetate buffer, pH 6, from 10 mM to 1M. rLDM TM 1, 2, 3, 4, 5, and 6 elute from the column in a typical preparation at the following sodium acetate molarities, respectively: 0.16, 0.18, 0.34, 0.40, 0.58, and 0.43M to give essentially pure rLDM TM 1-6. Each rLDM TM is substantially free of other rLDM TM and native proteins.

Characterization of the Novel rLDM TM

The rLDM TM have been characterized by the following criteria:

(1) ability to catalyze the oxidation of veratryl alcohol to veratrylaldehyde;
(2) molecular weight as determined by SDS-PAGE;
(3) amino acid composition;
(4) heme content;
(5) homology by antibody reactivity;
(6) specificity of activity against lignin model substrates; and
(7) elution from an FPLC column at specified sodium acetate molarities.

All of the rLDM TM catalyze the oxidation of veratryl alcohol to veratrylaldehyde, as monitored spectrophotometrically at 310 nm. A unit of activity is defined as the production of 1 micromole of veratrylaldehyde aldehyde in the rLDM TM catalyzed reaction. The specific activities of typical preparations at about 24° C. are as follows:

| rLDM TM | 1 | 2 | 3 | 4 | 5 | 6 |
|---|---|---|---|---|---|---|
| SPECIFIC ACTIVITY UNITS/MG · MINUTE | 2.6 | 17.1 | 5.1 | 9.7 | 9.4 | 12.4 |
| MOLECULAR WEIGHT kD | 38 | 38 | 42 | 42 | 43 | 42 |

Amino acid composition-See Table 1.

Heme and carbohydrate content--rLDM TM 1, 2, 3, 4, 5, and 6 each contain a single protoheme IX moiety. All are glycosylated according to periodic acid staining (PAS) and binding to Con A-Sepharose (Sigma).

Immunoblot Procedure

This procedure was used to further characterize the rLDM TM. It is a standard procedure which is disclosed in Towbin et al. (Towbin, H., Staehelin, T. and Gordon, J. [1979] Proc. Natl. Acad. Sci. USA 76: 4350). The procedure involves separating the proteins by electrophoresis in a gel, transfer of the proteins to a solid matrix, and reacting with (1) a primary probe, rabbit anti-rLDM TM antibody and (2) a secondary probe, goat anti-rabbit antibody coupled to horseradish peroxidase.

rLDM TM 1, 3, 4, 5, and 6 react to polyclonal antibodies made to rLDM TM 2 and 6, using the above immunoblot procedure. rLDM TM 2, in the same procedure, reacts to polyclonal antibodies made to rLDM TM 6.

All the rLDM TM disclosed herein have the following unique activities on lignin model substrates:

(1) oxidative cleavage of $C_\alpha-C_\beta$;
(2) hydroxylation of benzylic methylene groups
(3) oxidation of benzyl alcohols to aldehydes;
(4) phenol oxidation; and
(5) oxidation of methoxy and ethoxy benzene.

"Lignin model substrates" are chemicals which resemble parts of lignin. The above activities are characteristic of the rLDM TM disclosed herein.

Following are Examples which illustrate the best mode for practicing the invention. These Examples should not be construed as limiting. In all Examples herein, percentages are by weight and solvent mixture proportions are by volume unless otherwise noted.

EXAMPLE 1—TREATMENT OF TMP WITH rLDM TM AND OTHER LIGNINOLYTIC ENZYMES

The Ligninolytic Mixture TM, as described in Preparative Example 2, (0.15-1.5 mg protein total) was added to 10 gm of TMP (dry weight) at 3% consistency in 10 mM trans-aconitic acid, pH 4.5, 400 $\mu$M $H_2O_2$ and 100 $\mu$M $MnSO_4$. The pulp slurry was flushed with $O_2$ and incubated with slow shaking at 39° C. for 12 hr, after which time the TMP was washed with water. The tensile, tear and burst indices as well as breaking length of the pulp was measured and found to be of enhanced strength versus an untreated sample. The brightness reversion of the treated sample was less than the untreated sample; therefore, brightness stability was increased with the Ligninolytic Mixture TM treatment.

The use of $MnSO_4$ is optional.

Regarding the above conditions, for each of the parameters there is a range of values which can be used to achieve the desired result. Typical values and acceptable ranges for each parameter are shown in Table 2.

EXAMPLE 2 rLDM TM 1 through 6, individually, or mixtures thereof, can be used to treat TMP using essentially the same procedures as disclosed in Example 1, including ranges, or obvious modifications thereof. The resulting pulp is of high quality.

EXAMPLE 3

Upon substituting the Ligninolytic Mixture TM of Example 1 with extracellular growth medium, prepared as disclosed in Preparative Example 1, there is obtained pulp of high quality.

EXAMPLE 4

Upon substituting the Ligninolytic Mixture TM of Example 1 with a mixture comprising all of the following or any combination thereof: rLDM TM 1-6, individually or mixtures thereof; Ligninolytic Mixture TM ; and extracellular growth medium there is obtained pulp of high quality.

EXAMPLE 5

Upon substituting CTMP or CMP for the TMP in Examples 1-4, there is obtained pulp of high quality.

The rLDM TM of the subject invention can be used in the crude form, in a purified form, wherein each rLDM TM is substantially free of other rLDM TM and native proteins, and in mixtures thereof. It is well within the skill of a person skilled in the art to adjust amounts of rLDM TM used in accordance with the purity of the rLDM TM preparation.

"Native proteins" as used herein refers to other proteins present in the extracellular fermentation medium, as described above.

TABLE I

| | Amino Acid Composition of rLDM TM | | | | |
|---|---|---|---|---|---|
| Amino Acid | rLDM TM 1 Ratio | rLDM TM 2 Ratio | rLDM TM 3 Ratio | rLDM TM 5 Ratio | rLDM TM 6 Ratio |
| asp/asn | 1.4 | 2.0 | 5.4 | 5.0 | 3.0 |
| glu/gln | 6.0 | 7.7 | 16.8 | 19.9 | 8.0 |
| ser | 4.3 | 4.1 | 14.0 | 22.3 | 6.8 |
| his | 4.4 | 3.2 | 7.3 | 15.9 | 3.2 |
| gly | 6.5 | 5.7 | 24.0 | 44.7 | 8.3 |
| thr | 2.2 | 3.5 | — | — | 4.9 |
| arg | 1.1 | 1.2 | 2.9 | 4.8 | 1.3 |
| ala | 7.3 | 7.9 | 14.4 | 13.8 | 6.7 |
| tyr | 0.2 | — | 1.0 | 1.0 | 0.2 |
| met | — | — | 1.2 | — | 0.14 |
| val | 1.6 | 2.6 | 7.4 | 6.5 | 4.2 |
| phe | 1.1 | 3.0 | 7.0 | 3.3 | 3.2 |
| ile | 1.0 | 2.2 | 4.1 | 3.6 | 2.4 |
| leu | 1.5 | 2.6 | 6.5 | 6.0 | 3.3 |
| lys | 0.5 | 1.0 | 2.5 | 2.3 | 1.0 |

TABLE 2

| Parameter | Typical | Range |
|---|---|---|
| Consistency | 3% | 0.01 to 20%* |
| Ratio of Ligninolytic Mixture TM to mechanical pulps (mg of protein/g of pulp) | 0.08 | 0.015 to 0.15 |
| Concentration of trans-aconitic acid** | 10 mM | 0.005 to 0.5 M |
| pH | 4.5 | 2 to 7 |
| Concentration of $H_2O_2$ | 400 $\mu$M | 2 $\mu$M to 10 mM |
| Concentration of $MnSO_4$ | 100 $\mu$M | 10 to 500 $\mu$M |
| Incubation period | 12 hr | 2 min to 48 hr |
| Temperature during incubation | 39° C. | 15 to 50° C. |

*Concentrations greater than 20% can be used if the fluid consistency of the medium is maintained.
**Other nontoxic enzyme buffers such as ammonium tartrate can be used.

I claim:

1. A process for enhancing the strength properties and brightness stability of mechanical pulp which comprises treating said pulp with the Ligninolytic Mixture TM from a *Phanerochaete chrysosporium* fermentation consisting essentially of rLDM TM 1 through 6, and other ligninolytic enzymes.

2. A process, according to claim 1, wherein said *Phanerochaete chrysosporium* is the novel mutant strain designated SC26, having the identifying characteristics of NRRL 15978.

3. A process, according to claim 1, wherein said mechanical pulp is TMP, or CTMP or CMP.

4. A process for enhancing the strength properties and brightness stability of mechanical pulp which comprises treating said pulp with the extracellular growth medium from a *phanerochaete chrysosporium* fermentation consisting essentially of rLDM ™ 1 through 6, and other ligninolytic enzymes.

5. A process, according to claim 4, wherein said *Phanerochaete chrysosporium* is the novel mutant strain designated SC26, having the identifying characteristics of NRRL 15978.

6. A process, according to claim 4, wherein said mechanical pulp is TMP, CTMP or CMP.

7. A process for enhancing the strength properties and brightness stability of mechanical pulp which comprises treating said pulp with an rLDM ™ selected from the group consisting of rLDM ™ 1, rLDM ™ 2, rLDM ™ 3, rLDM ™ 4, rLDM ™ 5, and rLDM ™ 6, or mixtures thereof.

8. A process, according to claim 7, wherein said mechanical pulp is TMP, or CTMP or CMP.

9. A process for enhancing the strength properties and brightness stability of mechanical pulp which comprises treating said pulp with a mixture consisting essentially of one or more of the following: rLDM ™ 1 through 6, individually or a mixture thereof; Ligninolytic Mixture ™ from a fermentation of *Phanerochaete chrysosporium,* consisting essentially rLDM ™ 1 through 6, and other ligninolytic enzymes; and extracellular growth medium from a fermentation of *Phanerochaete chrysosporium* consisting essentially of rLDM ™ 1 through 6, and other ligninolytic enzymes.

10. A process, according to claim 9, wherein said *Phanerochaete chrysosporium* is the novel mutant strain designated SC26, having the identifying characteristics of NRRL 15978.

11. A process, according to claim 1, wherein said Ligninolytic Mixture ™ from a fermentation of *Phanerochaete chrysosporium* is added to mechanical pulp which is in about 2 $\mu$M to about 10.0 mM $H_2O_2$, buffered at about pH 2 to about pH 7, and has a consistency of about 0.01 to about 20%; said Ligninolytic Mixture ™ is added to said mechanical pulp in the ratio of about 0.015 to about 0.15 mg protein/g mechanical pulp (dry weight); the resulting slurry is then shaken at about 15° C. to about 50° C. for about 2 min to about 48 hr and washed with water, to obtain mechanical pulp with enhanced strength properties and brightness stability.

12. A process, according to claim 1, wherein said Ligninolytic Mixture ™ from a fermentation of *Phanerochaete chrysosporium* is added to mechanical pulp which is in about 400 $\mu$M $H_2O_2$, buffered at about pH 4.5, and has a consistency of about 3%; said Ligninolytic Mixture ™ is added to said mechanical pulp in the ratio of about 0.08 mg protein/g mechanical pulp (dry weight); the resulting slurry is then shaken at about 39° C. for about 12 hr and washed with water, to obtain mechanical pulp with enhanced strength properties and brightness stability.

13. A process, according to claim 4, wherein said extracellular growth medium from a fermentation of *Phanerochaete chrysosporium* is added to mechanical pulp which is in about 2 $\mu$M to about 10 mM $H_2O_2$, buffered at about pH 2 to about pH 7, and has a consistency of about 0.01 to about 20%; said extracellular growth medium is added to said mechanical pulp in the ratio of about 0.015 to about 0.15 mg protein/g mechanical pulp (dry weight); the resulting slurry is then shaken at about 15° C. to about 50° C. for about 2 min about 48 hr and washed with water, to obtain mechanical pulp with enhanced strength properties and brightness stability.

14. A process, according to claim 12, wherein said mechanical pulp is TMP.

15. A process, according to claim 13, wherein said mechanical pulp is TMP, or CTMP, or CMP.

16. A process, according to claim 1, wherein about 10 to about 500 $\mu$M $MnSO_4$ is added with the Ligninolytic Mixture ™.

17. A process, according to claim 2, wherein about 10 to about 500 $\mu$M $MnSO_4$ is added with the Ligninolytic Mixture ™.

18. A process, according to claim 16, wherein the concentration of $MnSO_4$ is about 100 $\mu$M.

19. A process, according to claim 17, wherein the concentration of $MnSO_4$ is about 100 $\mu$M.

20. A process, according to claim 4, wherein about 10 to about 500 $\mu$M $MnSO_4$ is added with the extracellular growth medium.

21. A process, according to claim 5, wherein about 10 to about 500 $\mu$M $MnSO_4$ is added with the extracellular growth medium.

22. A process, according to claim 11, wherein said *Phanerochaete chrysosporium* is the novel mutant strain designated SC26, having the identifying characteristics of NRRL 15978.

23. A process, according to claim 12, wherein said *Phanerochaete chrysosporium* is the novel mutant strain designated SC26, having the identifying characteristics of NRRL 15978.

* * * * *

UNITED STATES PATENT AND TRADEMARK OFFICE
CERTIFICATE OF CORRECTION

PATENT NO. : 4,687,745
DATED : August 18, 1987
INVENTOR(S) : Roberta L. Farrell

It is certified that error appears in the above-identified patent and that said Letters Patent are hereby corrected as shown below:

Title: "RLDM" should read --rLDM--.
Col. 1: line 1: "RLDM" should read --rLDM--.
Col. 2: line 1: "pulps" should read --pulps.--.
Col. 3: line 28: "$CaCl_2 2H_2O$" should read --$CaCl_2 \cdot 2H_2O$--; line 31: after "contains", insert --$7.8 \times 10^{-3}$ M nitriloacetic acid, $1.2 \times 10^{-2}$ M $MgSO_4 \cdot$--; line 32: "$CoC_2$" should read --$CoCl_2$--; $9.0 \times 10$-4 M" should read --$9.0 \times 10^{-4}$ M--; line 34: "$AlK(S_4)_2O$" should read --$AlK(SO_4)_2 \cdot 12H_2O$--.
Col. 4: line 1: "5000XG" should read --5000 xG--; line 34: delete "aldehyde".
Cla. 4: line 4: "*phanerochaete*" should read --*Phanerochaete*--.
Cla. 9: line 7: "essentially rLDMTM" should read-- essentially of rLDM$^{TM}$--.
Cla. 13: line 10: "2 min" should read --2 min to--.

Signed and Sealed this

First Day of March, 1988

Attest:

DONALD J. QUIGG

Attesting Officer

Commissioner of Patents and Trademarks